United States Patent [19]

Askwith et al.

[11] Patent Number: 5,031,456

[45] Date of Patent: Jul. 16, 1991

[54] METHOD FOR THE DETECTION OF VOIDS AND CORROSION DAMAGE BY THERMAL TREATMENT

[75] Inventors: Herbert H. Askwith, Singer Island; Allen E. Wehrmeister; Scott R. Clinton, both of West Palm Beach; Richard P. Milke, Lake Worth, all of Fla.

[73] Assignee: H.A.F.A. International, Inc., Riviera Beach, Fla.

[21] Appl. No.: 389,739

[22] Filed: Aug. 4, 1989

[51] Int. Cl.$^5$ .................... G01N 29/04; G01N 29/16
[52] U.S. Cl. ...................................... 73/587; 73/590; 73/592; 374/5
[58] Field of Search ................. 73/587, 590, 592, 801, 73/602; 374/5

[56] References Cited

U.S. PATENT DOCUMENTS

| | | | |
|---|---|---|---|
| 3,240,674 | 3/1966 | Ledwidge et al. | 376/245 |
| 3,264,863 | 8/1966 | Maropis | 73/522 |
| 3,946,600 | 3/1976 | Rettig et al. | 73/587 |
| 4,201,092 | 5/1980 | Dau | 73/587 |
| 4,274,288 | 6/1981 | Tittman et al. | 73/602 |
| 4,448,062 | 5/1984 | Peterson et al. | 73/587 |
| 4,459,851 | 7/1984 | Crostack | 73/587 |
| 4,472,971 | 9/1984 | Marini et al. | 73/587 |
| 4,499,769 | 2/1985 | Conway | 73/587 |
| 4,574,615 | 3/1986 | Bower | 73/24.01 |
| 4,609,994 | 9/1986 | Bassim et al. | 73/587 |

FOREIGN PATENT DOCUMENTS

| | | | |
|---|---|---|---|
| 0117447 | 7/1983 | Japan | 374/5 |
| 1265595 | 10/1986 | U.S.S.R. | 73/587 |
| 1280532 | 12/1986 | U.S.S.R. | 73/587 |

Primary Examiner—Hezron E. Williams
Assistant Examiner—Rose M. Finley
Attorney, Agent, or Firm—Lieberman, Rudolph & Nowak

[57] ABSTRACT

The present invention provides a method of detecting a void-related fault in a metal or metal alloy component. The method comprising filling the fault with a fluid, preferably liquid; treating the component and fluid so as to produce thermal-excitation in the component and fluid; and thereby cause a detectable acoustic signal. The detection of the signal detects the presence of a void-related fault. The invention also provides a method of locating and characterizing a void-related fault which comprises detection of the fault as described, measuring the parameters of the acoustic signal and the conditions for producing the signal, and correlating the parameters and conditions with the location and characteristics of the fault. The invention is particularly useful for the detection of microbiologically induced corrosion (MIC). The invention also concerns a method of evaluating a component for the severity of a void-related damage. The method comprises filling the void-related damage with a fluid (or maintaining the component in conditions so that the void-related damage is filled with the fluid); thermally treating the component and fluid so as to produce a detectable acoustic signal; evaluating parameters and conditions of the signal; and correlating the parameters and conditions with the severity of the damage.

17 Claims, 7 Drawing Sheets

FIG. 5
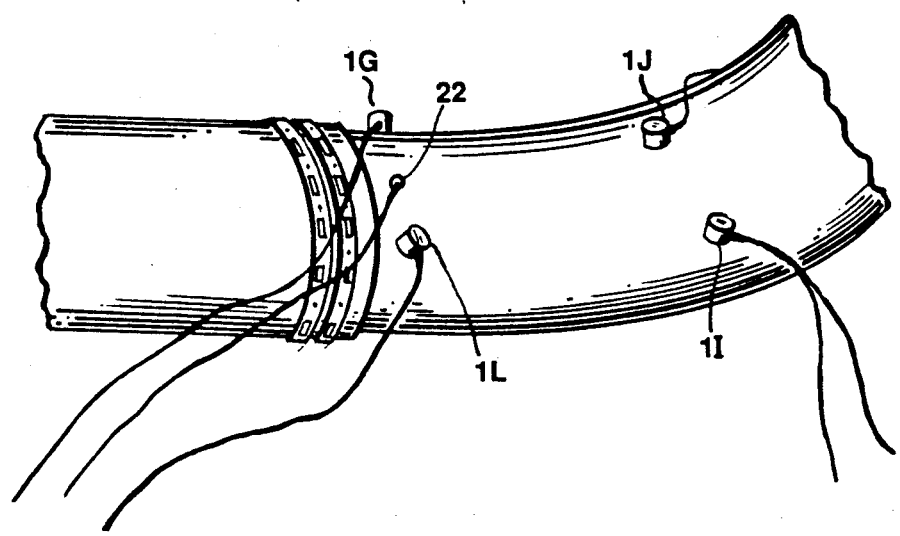
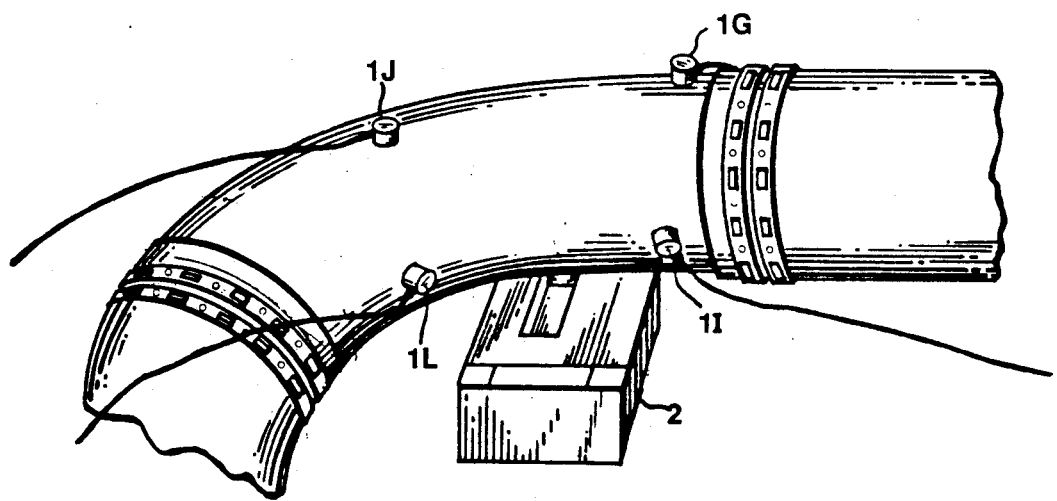
FIG. 6

METHOD FOR THE DETECTION OF VOIDS AND CORROSION DAMAGE BY THERMAL TREATMENT

This invention was made with government support under Contract No. 88NJR-44858B with the Tennessee Valley authority (TVA). The U.S. government may have certain rights in the invention.

BACKGROUND OF THE INVENTION

Microbiologically Induced Corrosion (MIC) [also referred to as Microbially Influenced Corrosion] is corrosion involving bacteria interacting with metal surfaces. Several bacterial species exist and cause corrosion with different combinations of materials and chemical constituents. By example, MIC is recognized in water filled and crude oil systems, attacking carbon steel and stainless steel. Generally described as pitting of the metal, MIC also produces cavern-like voids and tunnel-like voids within the metal which results in the overall reduction of metal thickness.

Chemical, electrochemical, and biological analysis of the fluid medium have been used to detect the presence of MIC in a system. Radiography has been used to detect MIC at its location in the metal. These techniques are time consuming and costly to implement or provide such limited information about the location and severity of MIC to make them ineffective for repairing the damage in metal systems caused by MIC. Faced with bacterially induced corrosion, system operators typically change the material of construction or implement elaborate programs to control the bacteria as a preventive technique.

The methodology of this invention is to thermally stimulate the fluid within the MIC produced cavity or pit, causing that fluid to flow and/or to boil. Both flowing fluid and boiling produce acoustic energy, detectable with the nondestructive test method known as acoustic emission. The acoustic energy detected during thermal stimulation leads to the detection, location, and severity of the MIC damage. This method is more cost effective than present detection techniques and permits corrective action in the form of immediate repair or planned future maintenance based on the severity of damage present.

Acoustic emission has been used to monitor piping systems and vessels (tanks) in a variety of industries. Pressurization is the dominant form of stress (stimulus) application. Heaters have also been used to test flywheels for cracks; the heating of spokes producing sufficient stress in critical regions to yield acoustic emissions if a crack had been present. Mechanical loading of components, as in a three point bending application or dead weight on a steel rod, is also a common stress technique.

Commercial equipment is available which uses a thermal (hot-tip) probe to measure conductivity and/or wall thickness and/or surface cracks, but it is based on thermal conductance away from the probe or from a heater probe to a receiver probe. The application of this method to the detection of corrosion such as MIC is not known to exist.

The present invention provides an efficient, accurate, and nondestructive method to detect the presence of MIC damage or other corrosion damage in components and systems. The invention also provides a technique to locate the position of MIC-damage in a component or system and to establish the severity of the MIC-damage, wherein severity is related to the volume of metal corroded and/or the depth to which the MIC has progressed towards the outer surface of the component.

The present invention also provides a technique to detect, locate and assess MIC severity when the system or component has been drained of its contents; but not dried to the extend of removing fluid from MIC damage sites. It may also be use on a variety of metallic materials with various geometries and various fluid contents. In addition, during use of the invention, the invention may be employed to detect damage mechanisms through acoustic sources such as cracking, boiling, fluid flow or material deformation as a result of heating or thermally straining the region in which damage exists.

SUMMARY OF THE INVENTION

The present invention provides a method of detecting a void-related fault in a metal or metal alloy component. The method comprising filling the fault with a fluid, preferably liquid; treating the component and fluid so as to produce thermal-excitation in the component and fluid; and thereby cause a detectable acoustic signal. The detection of the signal detects the presence of a void-related fault. The invention also provides a method of locating and characterizing a void-related fault which comprises detection of the fault as described, measuring the parameters of the acoustic signal and the conditions for producing the signal, and correlating the parameters and conditions with the location and characteristics of the fault. The invention is particularly useful for the detection of microbiologically induced corrosion (MIC).

The invention also concerns a method of evaluating a component for the severity of a void-related damage. The method comprises filling the void-related damage with a fluid (or maintaining the component in conditions so that the void-related damage is filled with the fluid); thermally treating the component and fluid so as to produce a detectable acoustic signal; evaluating parameters and conditions of the signal; and correlating the parameters and conditions with the severity of the damage.

BRIEF DESCRIPTION OF THE FIGURES

FIG. 5—Weld #14403 heater and sensor experimental setup.

FIG. 6—Weld #14403 heater and sensor experimental setup.

DETAILED DESCRIPTION OF THE INVENTION

Figure 1:
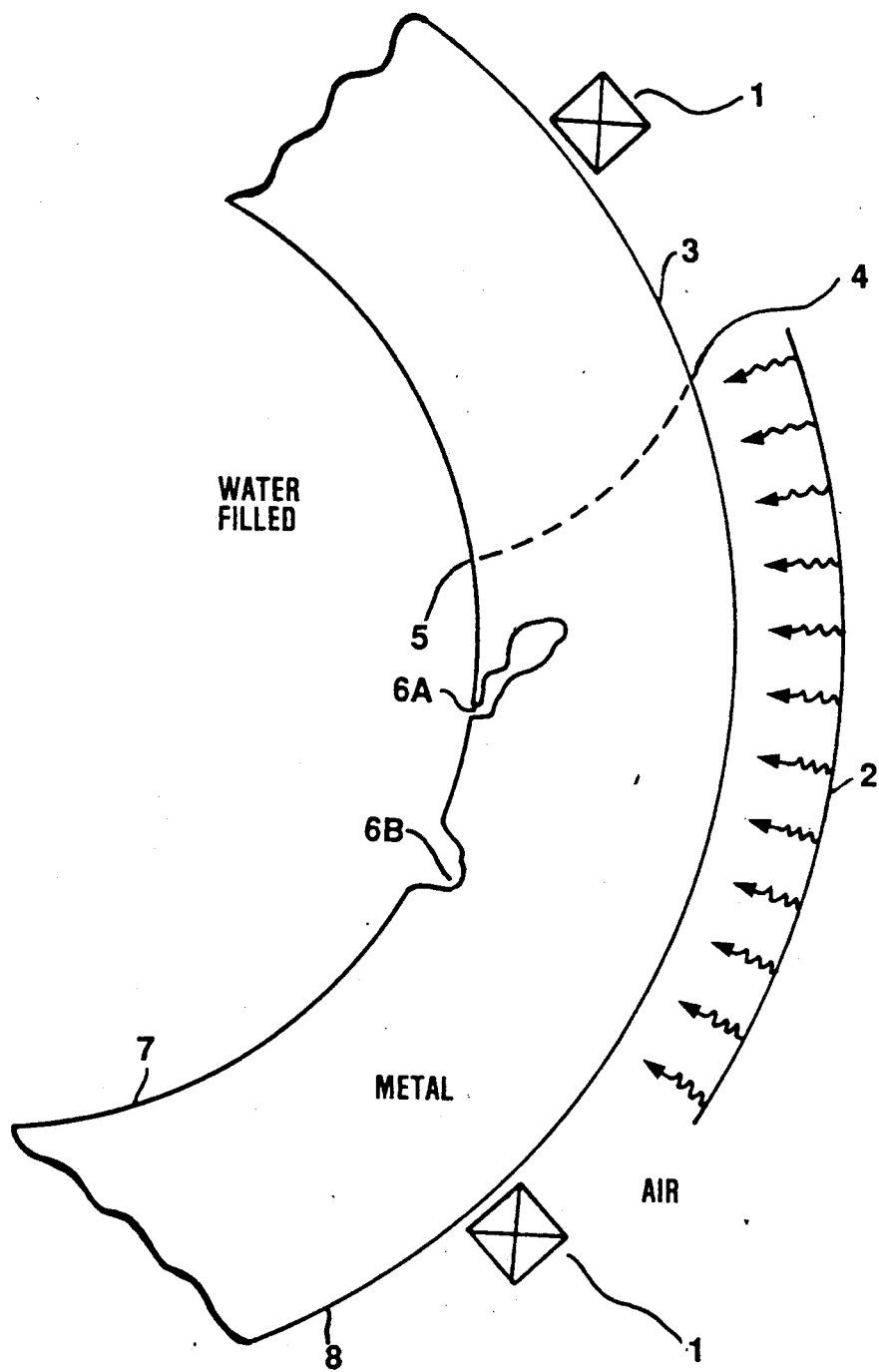
FIG. 1—Details of MIC damage in a piping component and typical setup for detection.

The present invention provides a method of detecting a void-related fault in a metal or metal alloy component which comprises:

a) filling the fault with a fluid;

b) treating the component and fluid so as to produce a thermal excitation in the component and fluid and thereby cause a detectable acoustic signal; and c) detecting the signal, thereby detecting the fault.

The method further involves locating and determining the characteristics or severity of a void-related fault in a metal or metal alloy component which comprises detecting the fault as described, measuring parameters of the acoustic signal and conditions for producing the signal, and correlating the parameters and conditions with the location and characteristics of the fault.

In the preferred embodiments, the metal or metal alloy component is a carbon steel or stainless steel component. However, the invention may also be practiced on a variety of materials including ceramics, glass, plastics and numerous metallic substances. The invention may also be practiced on a variety of components, such as piping walls, vessel walls, tank walls, or other components or structural configurations.

Typically, the component comprises two surfaces, an inner surface and an outer surface. In the preferred embodiments, the component defines an enclosed space such as the interior of a pipe, a vessel or a tank and the space is filled with a fluid, typically liquid. In such an embodiment, corrosion or other void-related damage mechanisms occur at the inner surface producing a void or cavity growing into the material towards the outer surface. The void-related damage may be in the form of pores, cracks, or cavities. The present invention may be practiced on such an arrangement by heating the outer surface of the component to produce a thermal gradient between the outer surface at a high temperature and the inner surface at a lower temperature. The heating causes thermal excitation or thermal stress which produces fluid flow, boiling, or other phenomenons which cause acoustic emissions. Detection, evaluation and characterization of the acoustic signals can be correlated to the presence, location and severity of the damage in the component. For instance, heating the outer surface to a temperature high enough to cause boiling of the fluid in the cavity produces acoustic emissions which can be correlated to the cavity in the material. The amount of heat input, the heating time and the time for initial boiling can be related to the distance between the cavity and the outer surface and the volume of the cavity. The heating is performed in a manner so as not to damage the component. If a plastic or other type component is being tested for which heating may be limited, selection of a fluid with a low boiling point may be necessary to practice the invention.

The present invention may be described in greater detail with reference to MIC-related damage in stainless or carbon steel piping. The following description is presented as an aid in understanding the present invention and is not intended to limit the present invention to the particular embodiment described.

The characteristics of damage caused by MIC in stainless or carbon steel piping include a narrow passage connecting the inner pipe surface with a water filled void in the pipe wall. It was speculated that, if a temperature gradient was established across the pipe wall, the differential expansion of the fluid within the cavity would cause a pressure gradient between the cavity and the inner pipe surface, resulting in a detectable leak-like flow. If the temperature gradient could be increased sufficiently to achieve boiling temperatures within the cavity, a flashing mechanism would be present, wherein the fluid would be maintained in a liquid state, even though above its boiling point, by the elevated pressure. At some point along the flow path, the fluid would reach saturation pressure and flash to a gas. Alternatively, the fluid may be brought to a boil within the cavity without significant increase in pressure and the gas may flow down the flow path. In either case, a flashing/boiling phenomenon and a detectable leak-like flow would result between the cavity and the inner pipe. Subsequently, upon losing heat to the fluid within the body of the piping, the gas, in bubble form, would return to a liquid state, resulting in bubble collapse.

Each of these mechanisms result in the release of energy in the form of high frequency sound. It was contemplated that existing commercial acoustic emission equipment would detect one or more of these mechanisms during the process of heating the material containing MIC, while material without MIC would remain "quiet" to the acoustic emission equipment.

The heat is applied to the side of the material opposite the side where MIC-damage may be present. For a pipe butt weld, by example, heat is locally applied to the outer diameter (O.D.) of the pipe over the circumference of the weld. The amount of heat available is controlled to achieve a thermal gradient between the O.D. and inner diameter (I.D.). The thermal gradient produces localized stress in the heated region and expansion of any fluids within MIC damaged areas. This results in the generation of acoustic emissions from phenomenons such as fluid flow, boiling, pre-existing cracks, and material deformation of corrosively-thinned regions. The acoustic emissions are related to the presence of MIC-damage. The level of heat is not damaging to the material and the material does not produce these acoustic sources when MIC-damage is not present.

As the temperature of the metal at any point throughout the metal thickness reaches the boiling point of the fluid, the formation and collapse of gas bubbles will cause acoustic emissions which indicate the presence of MIC. Boiling will occur either directly at the metal-to-fluid interface or at a point nearer the I.D. of the material if the fluid is at a high pressure in a cavity and flows to a lower pressure and flashes to gas.

The acoustic sources are detected with acoustic emission equipment. The cumulative energy of these signals and the rate of signals detected and/or signal energy rate as a function of heating time relate to the presence of MIC and its severity. Discrete events of acoustic sources can be located with acoustic emission equipment by measuring signal arrival time at two or more sensors.

Each of these parameters (signal rate, time, heat rate, temperature, signal amplitude, duration, energy (defined by ASTM standards as Measured Area of the Rectified Signal Envelope "MARSE"), cumulative event or hit rate, material thickness, heater-to-material spacing, material thermal conductivity, fluid type and its boiling point, and combinations thereof, relate to the detection of MIC, its location and severity assessment.

Figure 2:
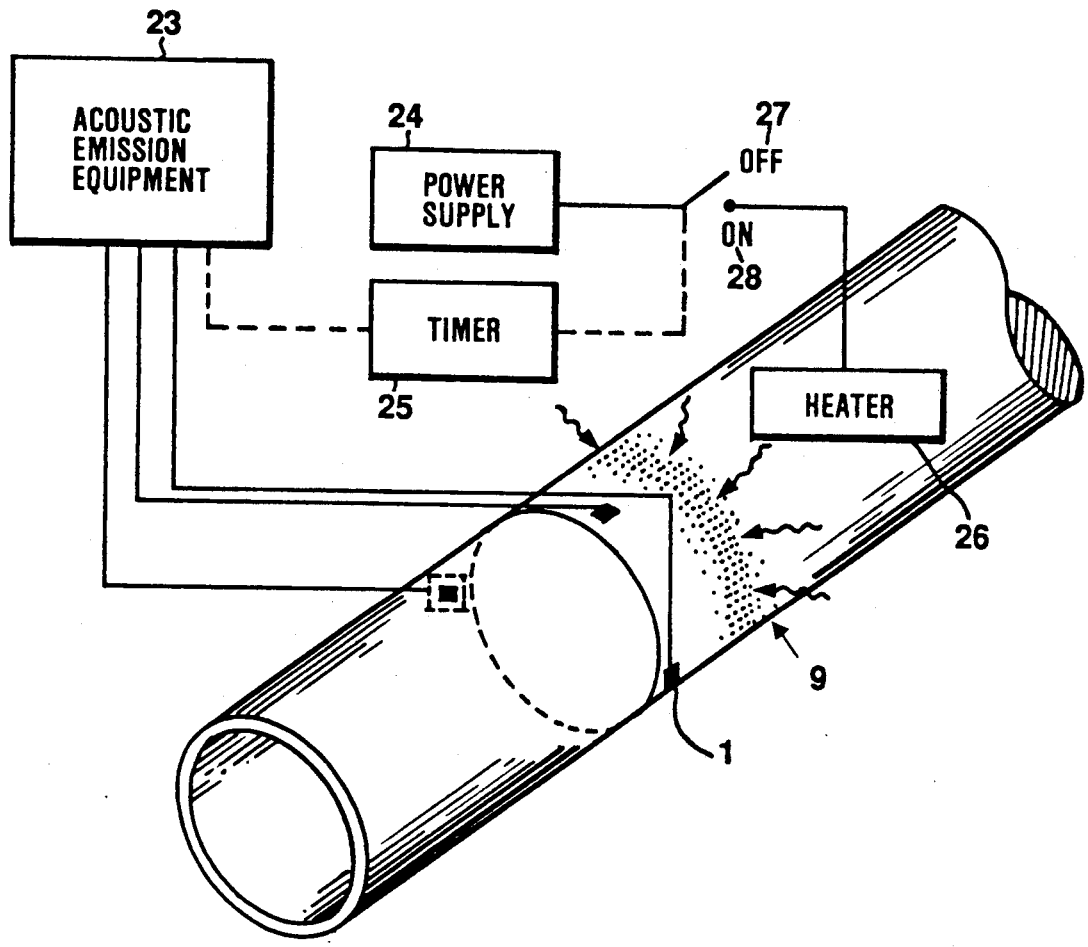
FIG. 2—Typical setup for MIC detection in piping.
Figure 3:
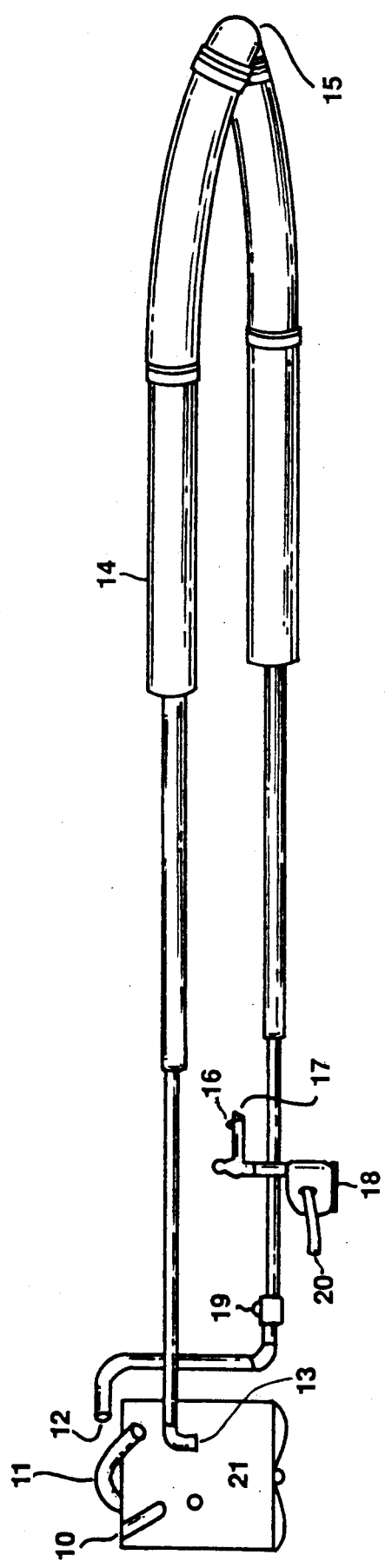
FIG. 3—Experimental test loop configuration for MIC-damaged piping used during development.
Figure 4:
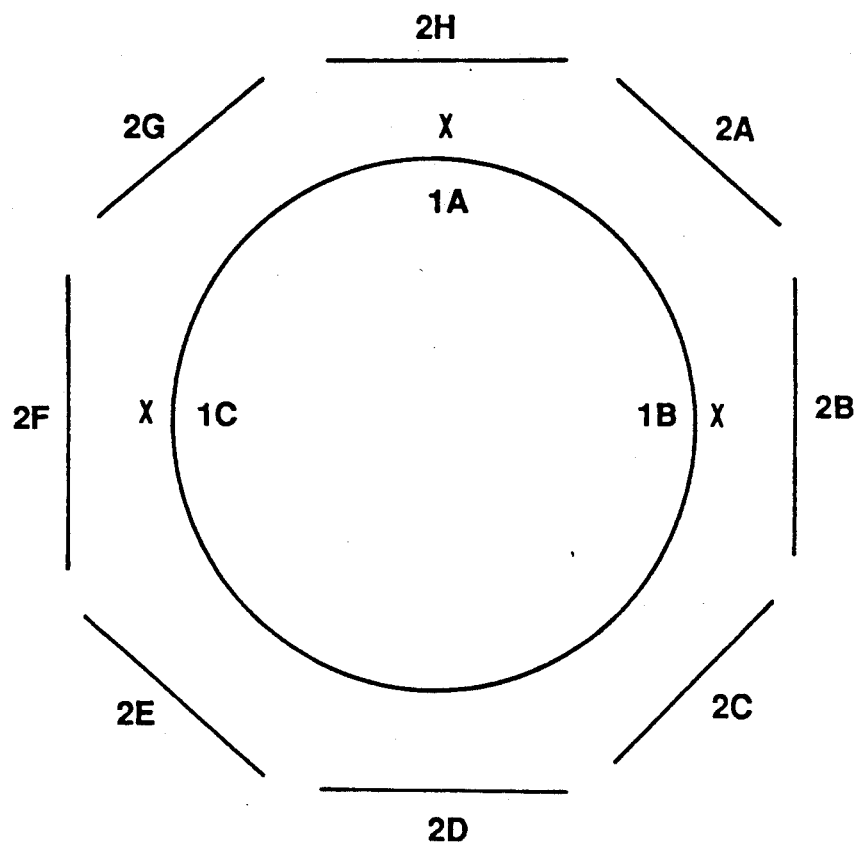
FIG. 4—Experimental heater and sensor locations for MIC-damage piping test.
Figure 7:
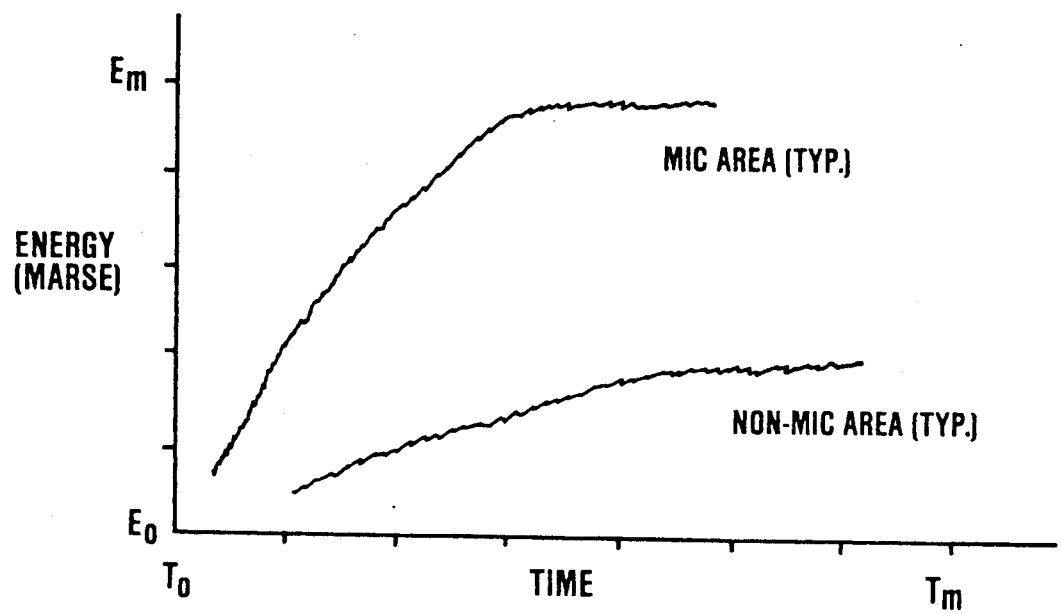
FIG. 7—Typical energy (MARSE) versus time graph for MIC and non-MIC areas.
Figure 8:
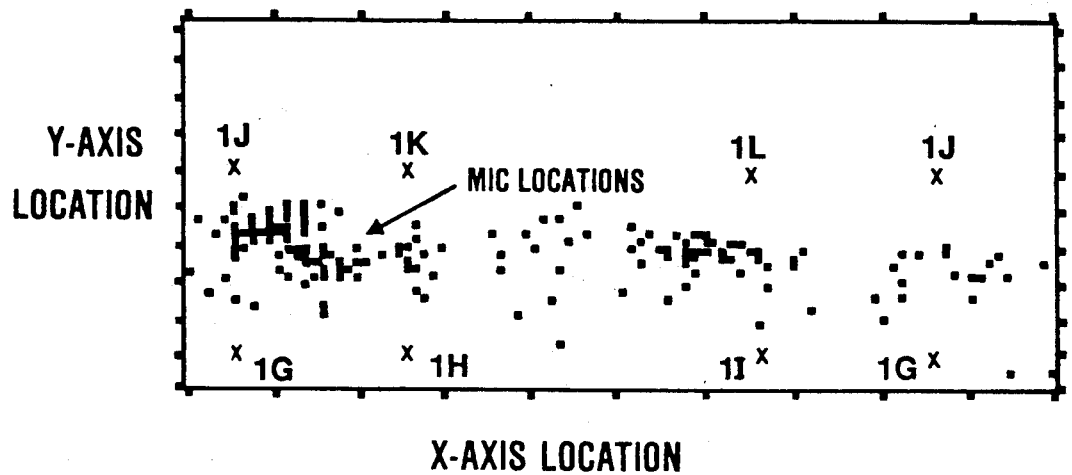
FIG. 8—Locational plot for weld #14403.
Figure 9:
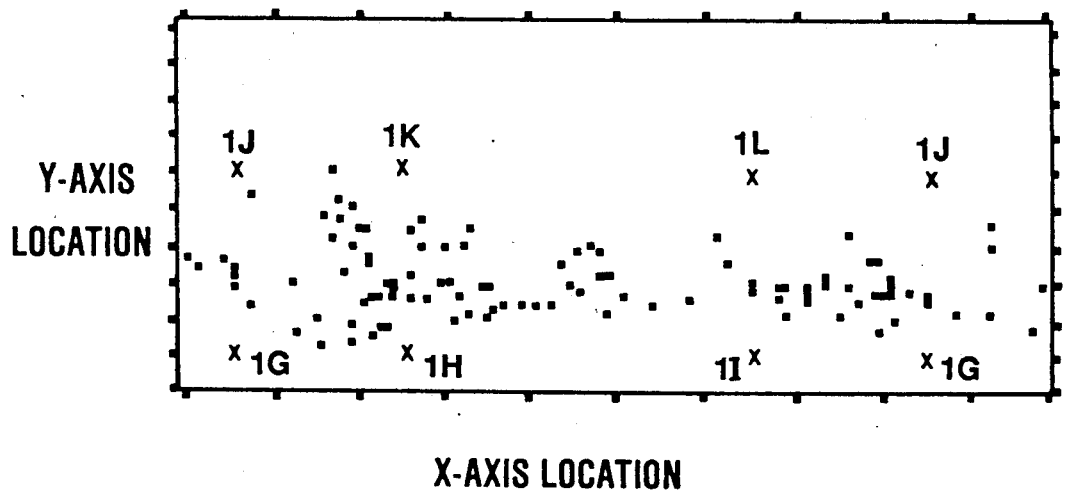
FIG. 9—Locational plot for weld #12317.

FIGS. 1 and 2 depict a typical setup for the MIC detection, location, and severity test. FIG. 1 shows details of MIC damage in a piping component and typical set-up for detection. Number 1 depicts acoustic emission sensors; 2 depicts a heat source; 3 depicts a temperature gradient with 4 representing a temperature greater than boiling and 5 representing a temperature equal to or less than boiling; 6A depicts typical MIC damage in stainless steel; 6B depicts typical MIC damage in carbon steel; 7 represents the inner diameter (I.D.); and 8 represents the outer diameter (O.D.). The I.D. of the piping component is water filled; the component is made of metal and the O.D. is surround by air. FIG. 2 shows typical set-up for MIC detection in piping. Number 23 represents acoustic emission equipment; 24 represents a power supply; 25 represents a timer; 27 and 28 represent the off and on positions of a switch, respectively; 26 represents a heater; 9 represents a weld; and 1 represents one of the three acoustic emission sensors (black boxes). In each case, the attainment of boiling temperature at the outermost surface of these cavities (pits) causes acoustic emissions. The time to achieve a boiling temperature at the damaged surface is related to the depth of damage, while the amount of acoustic activity is related to the volume of surface exposed to boiling temperature. High A.E activity rates and location indications are indicative of MIC detection. FIG. 3 shows an experimental test loop configuration for MIC damaged piping used during development. Number 10 depicts a pump bypass; 11 depicts a pump suction tube; 12 depicts a test loop discharge; 13 depicts a test loop inlet; 14 represents a vent valve; 15 depicts a 6″ stainless steel pipe section with MIC; 16 represents pump discharge to LMO; 17 depicts a bypass to the reservoir; 18 depicts a Worthington pump, model: 1 CN-22; 19 depicts a gate valve; 20 represents pump suction from the reservoir; and 21 depicts the reservoir. FIG. 4 shows an experimental heat and sensor locations for MIC-damage piping weld test. Numbers 1A, 1B and 1C represents sensor locations on one side of weld; 1D, 1E and 1F (not shown) correspond to symmetrically opposed locations, on the other side of the weld; numbers 2A-2H represent heat source locations. FIG. 5 shows a weld (#14403) heater and sensor experimental set up. 1G, 1H, 1J and 1K depict acoustic emission sensors and 22 depicts a thermocouple. FIG. 6 shows a weld (#12203) heater and sensor experimental set up. Numbers 1G, 1I, 1J and 1L depict acoustic emission sensors; 2 represents a heat source depicted as a heat lamp. FIG. 7 shows typical energy (MARSE) verses time graph for MIC and non-MIC areas. FIGS. 8 and 9 show locational plots for welds (#14403) and (#12317) respectively, which correspond to the acoustic emission sensor locations shown in FIGS. 5 and 6. Numbers 1G, 1H, 1I, 1J, 1K and 1L represent acoustic emission sensor locations; and the black squares represent MIC locations. All of the above figures are illustrative of the subject invention.

The following Experimental Detail section and examples are presented as illustrations of the invention and are not intended to, and should not be construed to, limit in any way the invention as set forth in the claims which follow thereafter.

EXPERIMENTAL DETAILS

In stainless steel piping, MIC is found predominantly in the welds and associated "heat affected zones", those areas extending outside the weld itself on either side to a distance or approximately four times the thickness of the pipe wall and whose material properties have been affected by the heat of the welding process. The primary detection technique, at present, is radiography. The radiographs of the test welds were utilized to verify the data obtained.

The data acquired on each test weld was divided into eight sections, based upon the position of the heat source used, a quartz lamp of nominally 3000 watt output. The data is graphically presented as energy (MARSE) (a measure of the volume under the acoustic waveform envelope) over time (FIG. 7 is a typical graph) and as locatable signal plot (designated as "-axis Location" vs. "X-axis Location") (FIGS. 8 and 9 are typical).

The welds examined were straight to elbow joints in sections of six inch, 316/316L stainless steel piping, respectively designated #14403 and #12317. In both welds, the variation of data between a MIC-containing and a non-MIC areas is most apparent. See FIGS. 7, 8 and 9. The energy (MARSE) graph for the non-MIC area indicates a level substantially less than that for the MIC area (FIG. 7). Likewise, the locational plots show few locatable events for the non-MIC areas while the MIC area shows a high concentration of events (FIGS. 8 and 9). The MIC locations indicated in both of these welds correspond to the MIC locations shown by the radiographs.

EXAMPLES

A series of experiments were performed utilizing acoustic emission (AE) techniques in order to determine the ability of AE to detect Microbiologically Induced Corrosion (MIC) within a section of six-inch diameter stainless steel type 316L pipe. Based on the results of these experiments, it was determined that the acoustic emission technique could be used for the detection and location of MIC in weld regions.

Two test specimens including welds #14403 and #12317 were used for this purpose. Each test specimen was placed into a loop configuration, as illustrated in FIG. 3, and filled with water to simulate plant conditions.

The acoustic emission system used was Physical Acoustics Corporation (PAC) Spartan Acoustic Emission System with a multi-channel electronic monitoring system and a PAC 3000 computer and associated software. In conjunction with the unit, eight PAC R-15 sensors and associated preamplifiers were initially used. The number of sensors was later reduced to six and found to be more than adequate for locational capability. The sensors were mounted to the test specimens using adhesive couplant in such a way as to provide ample coverage of the weld, for it was not known at that time what the data would show or how many times it would reproduce itself. After installing the sensors and connecting all associated cabling, a verification of each sensor was performed by breaking a 0.3 mm lead at each sensor. Also at this time, taps on the weld were performed to verify locational accuracy of the rectangular sensor array.

The heat source used was an Emerson Electric Company 1.5 kilowatt heater lamp, Model 1000T-3. A preliminary heatup experiment was performed by heating a similar test piece while monitoring temperature. Two thermocouples were attached to the test piece, one on the outer wall and one on the inner wall. The heat lamp was then positioned at 1.5 inches away from the test piece and heat applied. Temperature increase was monitored at both locations (inner and outer walls) against time until the inner wall reached 211° F. With the heat lamp 1.5 inches away it took 5 minutes, 23 seconds, for the temperature of the inner wall to reach 211° F. with an outer wall temperature of 226° F. This experiment was performed on a section of pipe without any water in it; an additional 1500 watt bulb was added to increase the heat output of the lamp to compensate for water present in the pipe during the demonstration.

An additional experiment was performed to check the heat output of the lamp with the additional 1500 watt bulb to determine the surface temperature of a dry pipe. Beginning with an ambient temperature of 78.6° F., the lamp was turned on and the temperature monitored for three (3) minutes, after which an outer surface temperature of 744° F. was recorded.

AE data was monitored while heating the welds at prescribed location circumferentially around the test specimen as shown in FIG. 4. Data was acquired for a total of eight different times at eight different heater locations. Each data set consisted of a three minute heat-up time followed by a two minute cool-down, for a total data acquisition time of five minutes. Using this sequence, the entire circumference of the weld was heated and tested and the data recorded. FIGS. 5 and 6 show sensor setup and the heating arrangement in heater location 10 for weld #14403, typical.

The test data was analyzed using the SPP/DAQ software from PAC. Plots were generated for each data run. The graph shown in FIG. 7 depicts cumulative energy versus time, which in this case shows that greater energies over a shorter period of time typically depicts an area of MIC, whereas lower energy over a longer period of time is associated with an area containing no MIC. The graphs of FIGS. 8 and 9 depict a rectangular sensor array which was used for the purpose of analyzing the location of AE sources. Areas containing MIC typically produced locatable events whereas non-MIC areas produced very few, if any, locations.

The graph information indicates areas of MIC-damage which was confirmed by x-ray overlays. Weld #1403 (FIG. 8) has three (#3) MIC areas and weld #12317 (FIG. 9) has two (2) MIC areas.

What is claimed is:

1. A method of locating and characterizing a void-related fault filled with a fluid in an area of a component which comprises:
   a) connecting a plurality of sensors to the component in predetermined locations so as to be able to detect and measure acoustic signals produced in the area of the component;
   b) thermally treating the component in such an manner so as to produce a detectable acoustic signal at the void-related fault;
   c) simultaneously detecting and measuring the parameters of the detectable acoustic signal at each of the sensors;
   d) evaluating and correlating the parameters of the acoustic signals and the locations of the sensor with the location and characteristic of the void-related fault.

2. A method of claim 1, wherein the component comprises a metal or metal alloy.

3. A method of claim 2, wherein the metal or metal alloy is a carbon steel or a stainless steel.

4. A method of claim 1, wherein the component has two surfaces and wherein the treating of step (b) comprises creating a thermal gradient between the surfaces.

5. A method of claim 4, wherein the void-related fault is a cavity having a passage to at least one surface.

6. A method of claim 5, wherein the metal or metal alloy component is a piping wall, a vessel wall, or a tank wall.

7. A method of claim 6, wherein the fluid is a liquid.

8. A method of claim 7, wherein treating comprises heating one surface to produce a thermal gradient between the surfaces, the high temperature and thermal gradient being sufficient to boil the liquid in the cavity or passage.

9. A method of claim 8, wherein the detectable acoustic signal comprises acoustic emissions caused by boiling of the liquid in the cavity or passage.

10. A method of claim 9, wherein the cavity is caused by microbiologically induced corrosion (MIC).

11. A method of claim 10, wherein the characteristics of the fault comprise volume of the cavity and depth of the cavity from one of the surfaces.

12. A method of evaluating a component for severity of void-related damage which comprises:
   (a) filling the void-related damage with a fluid;
   (b) thermally treating the component and fluid so as to produce a detectable acoustic signal;
   (c) measuring simultaneously the parameters of the acoustic signal at a plurality of monitoring points and evaluating the treatment conditions for producing the signal; and
   (d) correlating the parameters and conditions to determine the severity of the damage.

13. A method of claim 12, wherein the void-related damage comprises pores, cracks, or cavities caused by corrosion.

14. A method of claim 13, wherein the corrosion is MIC-related.

15. A method of claim 13, wherein treating is performed by heating the component to boil the fluid in the void-related damage and detecting acoustic emissions caused by the boiling.

16. A method of claim 12, wherein the component comprises a metal or metal alloy.

17. A method of claim 16, wherein the metal or metal alloy is a carbon steel or stainless steel.

* * * * *